US00PP32974P2

(12) United States Plant Patent
Grazzini

(10) Patent No.: US PP32,974 P2
(45) Date of Patent: Apr. 13, 2021

(54) ***NEPETA* PLANT NAMED 'G19213'**

(50) Latin Name: *Nepeta faassenii*
Varietal Denomination: G19213

(71) Applicant: Garden Genetics, Bellefonte, PA (US)

(72) Inventor: Richard A. Grazzini, Bellefonte, PA (US)

(73) Assignee: Garden Genetics LLC, Bellefonte, PA (US)

( * ) Notice: Subject to any disclaimer, the term of this patent is extended or adjusted under 35 U.S.C. 154(b) by 0 days.

(21) Appl. No.: 16/912,208

(22) Filed: Jun. 25, 2020

(51) Int. Cl.
*A01H 5/02* (2018.01)
*A01H 6/50* (2018.01)

(52) U.S. Cl.
USPC ..... Plt./263.1
CPC ..... *A01H 6/50* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Nepeta* plant named 'G19213' is disclosed, characterized by plants with a compact and densely branched habit, producing thick, dark green leaves. Vernalization is not required for flowering. Flowers are large, about double the typical size for this species and dark violet-blue. Plants flowering over a long period of time, from Spring through the first frost. The new cultivar is a *Nepeta*, suitable for ornamental garden purposes.

3 Drawing Sheets

Figure 1:
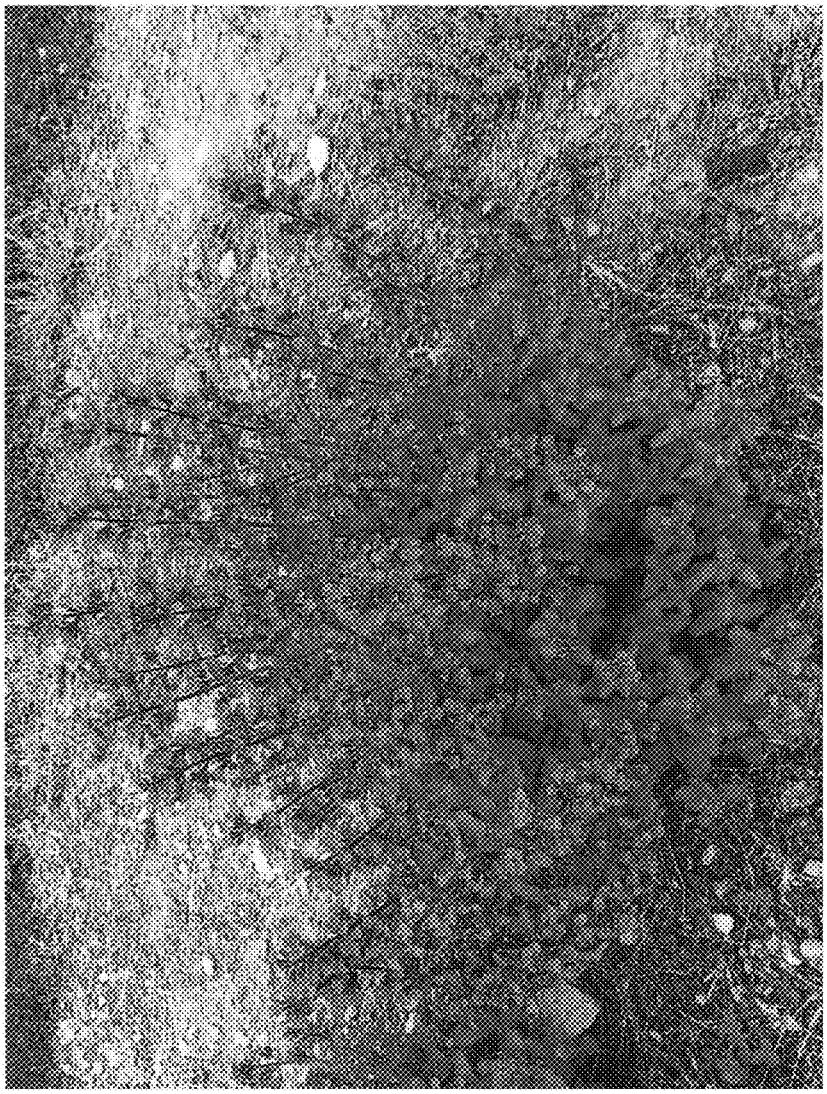

Latin name of the genus and species: *Nepeta faassenii*.
Variety denomination: 'G19213'.

BACKGROUND OF THE INVENTION

The new cultivar is a product of chance discovery by the inventor. This new variety, hereinafter referred to as 'G19213', was discovered as the result of a planned breeding program conducted by the inventor in Bellefonte, Pa. The seed parent is the variety *Nepeta faassenii* 'Walker's Low', unpatented. The pollen parent is *Nepeta faassenii* 'Psfike', U.S. Plant Pat. No. 18,904. The crossing resulting in the new variety was conducted August 2017 and selection of the new variety July 2018.

After identifying the new variety as a potentially interesting selection, the inventor first propagated 'G19213' by vegetative terminal stem cuttings during July of 2018, at a research greenhouse in Bellefonte, Pa. The inventor continued controlled testing and propagation, assessing stability of the unique characteristics of this variety. Subsequently, several generations have been asexually reproduced and have shown that the unique features of this cultivar are stable and reproduced true to type.

SUMMARY OF THE INVENTION

The cultivar 'G19213' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'G19213' These characteristics in combination distinguish 'G19213' as a new and distinct *Nepeta* cultivar:

1. Thick, dark green leaves.
2. Large dark violet-blue florets, about double typical size.
3. Season-long flowering.

4. No vernalization required for flowering.
5. Compact and densely-branched plant habit.

COMPARISON TO PARENT VARIETIES

'G19213' is similar in most horticultural characteristics to the seed parent variety. Plants of the new cultivar 'G19213' however, differ in the following:

1. The new variety grows less vigorously than 'Walker's Low'.
2. The new variety produces shorter, denser inflorescences than the seed parent.
3. Foliage of the new variety is darker green.
4. Florets color of the new variety is darker violet-blue than the seed parent.

'G19213' is similar in most horticultural characteristics to the pollen parent variety. Plants of the new cultivar 'G19213' however, differ in the following:

1. The new variety grows more vigorously than 'Psfike'.
2. The new variety produces longer inflorescences than the pollen parent.
3. Florets of the new variety are larger than those of the pollen parent.
4. Florets color of the new variety is darker violet-blue than the pollen parent.
5. Plant habit of the pollen parent is more compact than the new variety.

COMMERCIAL COMPARISON

'G19213' can be compared to the commercial variety *Nepeta* 'Cat's Meow', U.S. Plant Pat. No. 24,472. Plants of the new cultivar 'G19213' are similar to plants of 'Cat's Meow' in most horticultural characteristics. Plants of the new cultivar 'G19213' however, differ in the following characteristics:

1. New variety is more compact than 'Cats Meow'
2. New variety has larger florets than 'Cats Meow'
3. Florets of new variety are darker violet-blue in color than 'Cats Meow'
4. New variety had darker green foliage than 'Cats Meow'
5. New variety has thicker and more wrinkled leaves than 'Cats Meow'

'G19213' can be compared to the known commercial variety *Nepeta* 'Kitten Around', U.S. Plant Pat. No. 30,940. Plants of the new cultivar 'G19213' are similar to plants of 'Kitten Around' in most horticultural characteristics. Plants of the new cultivar 'G19213' however, differ in the following characteristics:

1. New variety is more vigorous and less compact than 'Kitten Around'
2. New variety has larger florets than 'Kitten Around'
3. Florets of new variety are darker blue in color than 'Kitten Around'
4. New variety has darker green foliage than 'Kitten Around'
5. Leaves of new variety are thicker and more wrinkled than those of 'Kitten Around'

BRIEF DESCRIPTION OF THE PHOTOGRAPHS

The accompanying photograph in FIG. 1 illustrates in full color a typical overwintered plant of 'G19213' grown outdoors in the ground in Bellefonte, Pa. The plant is approximately 18 months.

Figure 2:
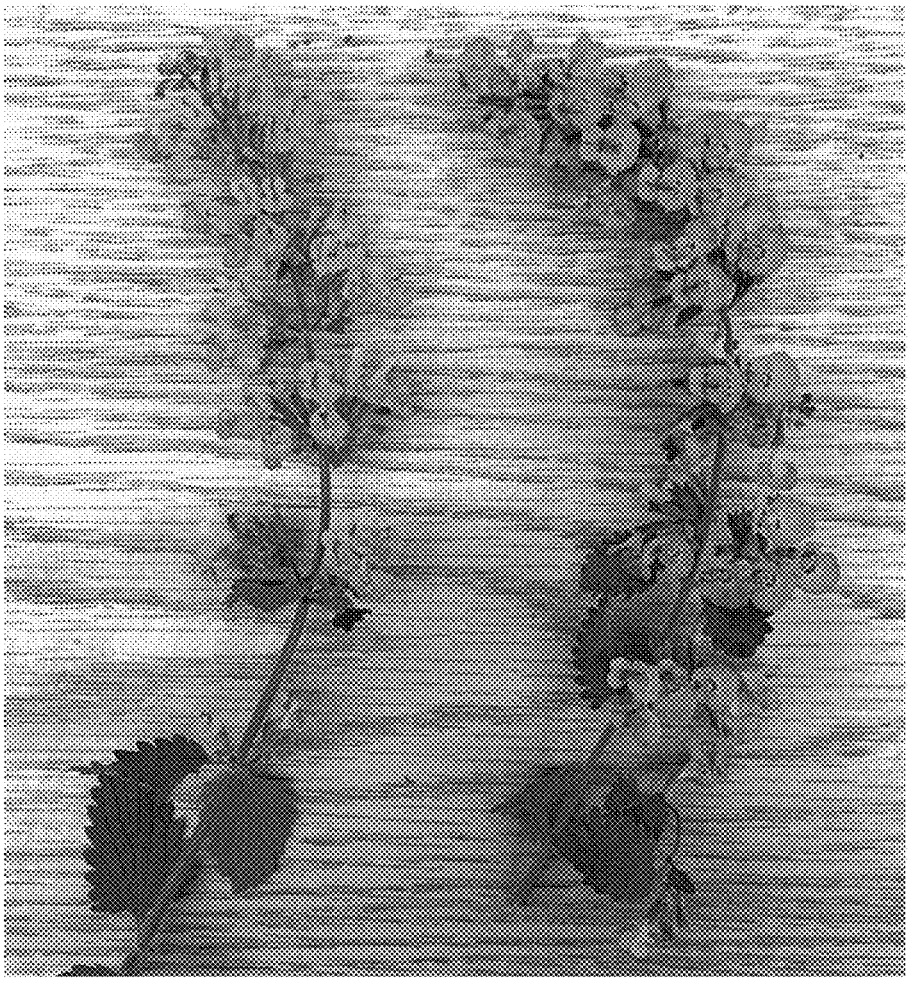

FIG. 2 shows a close up of a flowering spike of the new variety and of a comparator. The flowering spike of 'G19213', with more florets in a denser arrangement and darker florets is on the right side. The flowering spike on the left side is from the comparator 'Cats Meow'.

Figure 3:
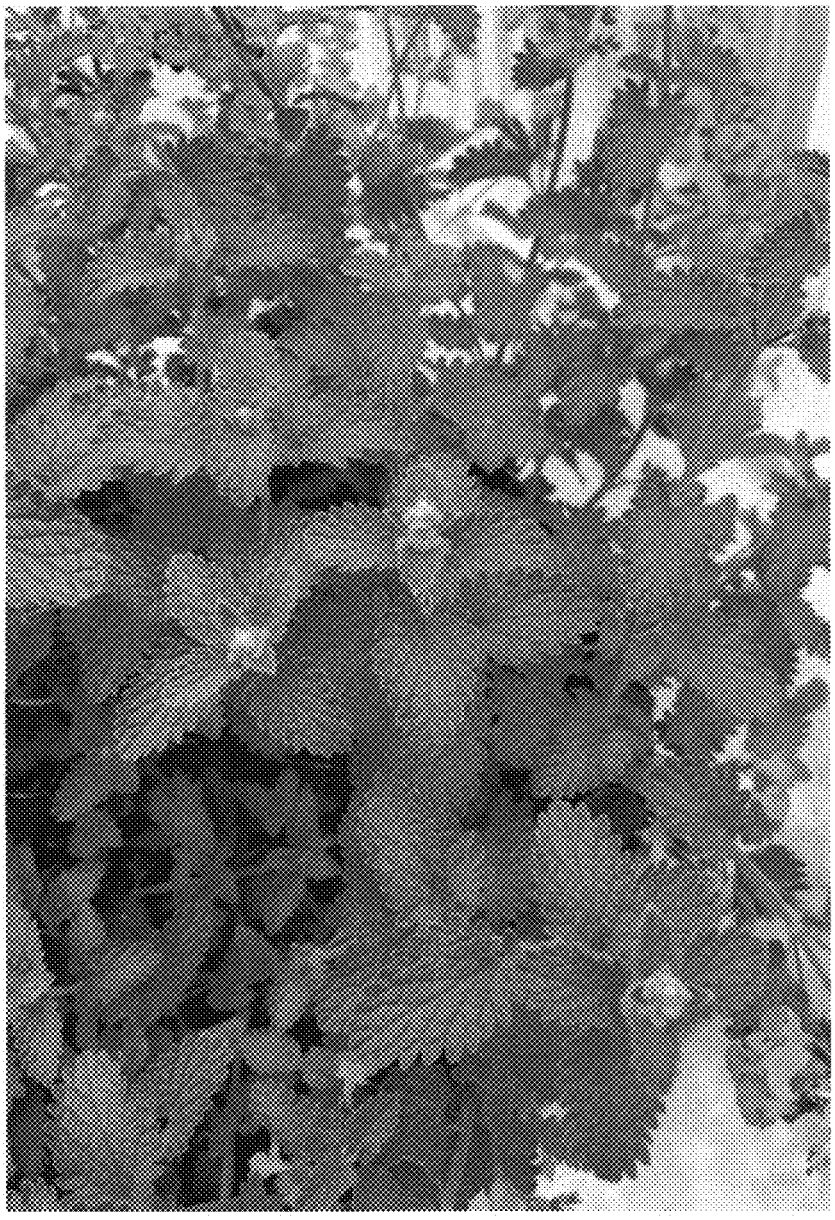

FIG. 3 illustrates in close up perspective of typical foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'G19213' plants grown outdoors in West Sussex, England. Plants are approximately 1 year old, in a 2 liter nursery container. Measurements and numerical values represent averages of typical plant types.

Botanical classification: *Nepeta faassenii* 'G19213'.

PROPAGATION

Time to initiate roots: About 5 days at approximately 16° C.
Time to produce a rooted cutting: About 14 days at 16° C.
Typical propagation method: Vegetative cuttings.

PLANT

Overall plant shape or growth habit: Upright, clump forming flowering perennial.
Plant spread: Approximately 30 cm.
Plant height: Approximately 17 cm to top of foliar plane. About 24 cm to top of flowering plane.
Growth rate: Moderate.
Length of primary lateral branches: Average range 9 to 18 cm.
Diameter of lateral branches: Approximately 3 mm.
Quantity of lateral branches: About 30.
*Color*.—Near RHS Green 138B.
*Texture*.—Softly pubescent.
Internode length: Average range 1.0 to 2.5 cm.
Age of plant described: Approximately 8 to 10 weeks from a rooted cutting.
Root description: Fine, fibrous, dense. Tan or white, not accurately measured with a color chart.

FOLIAGE

Leaf:
*Arrangement*.—Opposite.
*Quantity*.—Average range 10 to 16 per main branch.
*Average length*.—Approximately 2.5 cm.
*Average width*.—Approximately 1.5 cm.
*Shape of blade*.—Ovate.
*Apex*.—Broad acute.
*Base*.—Cordate.
*Attachment*.—Petiolate.
*Margin*.—Crenulate.
*Aspect*.—Undulating.
*Texture of top surface*.—Rugose, pubescent.
*Texture of bottom surface*.—Rugose, pubescent.
*Foliage scent*.—Strongly aromatic, typical fragrance for the species.
*Color*.—Young foliage upper side: Near RHS Green 137A. Young foliage under side: Near RHS Green 138A. Mature foliage upper side: Between Green 137A and 139A. Mature foliage under side: Near RHS Green 138A.
*Venation*.—Type: pinnate. Venation color upper side: Near RHS Green 137A. Venation color under side: Near RHS Green 138B.
*Petiole*.—Average Length: Approximately 6 mm. Diameter: Approximately 2 mm. Color: Near RHS Green 138B. Texture: Pubescent.

FLOWER

Natural flowering season: May to first hard frost(at the breeder's location, Bellefonte, Pa.)
Inflorescence type and habit: Terminal racemes with axially cymes subtended by reduced foliage-like bracts.
Individual flower longevity on plant: About 3 to 5 days.
Quantity of flowers: About 12 blooming spikes per plant at this age of maturity. About 60 to 100 florets per inflorescence.
Inflorescence size:
*Diameter*.—Approximately 4.1 cm.
*Height*.—Average range 14 to 18 cm.
Pedicel:
*Length*.—Average range 3 to 7 mm.
*Diameter*.—1.5 mm.
*Texture*.—Pubescent.
*Color*.—Near RHS Green 137C, sometimes flushed Greyed-Purple N186B.
*Orientation*.—Approximately 45 degrees angle of emergence. Straight.
*Strength*.—Strong and flexible.

Peduncle:
*Length*.—Average range 2 to 4 cm.
*Diameter*.—3 mm.
*Texture*.—Pubescent.
*Color*.—Near RHS Green 137D.
*Orientation*.—Approximately 0 to 15 degrees angle of emergence, straight to strongly undulating.
*Strength*.—Strong and flexible.

Individual flowers:
*Petal arrangement*.—The corolla is sympetalous and typically bilabiate with 2 small, highly fused lobes forming an upper lip and 3 larger highly fused lobes forming a lower lip.

Size:
*Diameter*.—Approximately 1.2 cm.
*Length*.—Approximately 1.6 cm.
*Persistence*.—Non-persistent.
*Fragrance*.—Musty.

Petals:
*Margin*.—Shallow and infrequently crenate at lower and upper lips.
*Tip shape*.—Upper lip: slightly reflexed. Lower lip: slightly cupped.
*Length*.—Upper lip: 6 mm. Lower lip: 10 mm. Tube: 1 cm.
*Width*.—Upper lip: 7 mm. Lower lip: 13 mm. Tube: 3 mm.
*Texture*.—Upper lip: pubescent on outer surface, glabrous on inner surface. Lower lip: pubescent on outer surface, glabrous on inner surface. Tube: pubescent.

Color:
*Upper lip*.—When opening: Inner surface: Near RHS Violet-Blue 90A. Outer surface: Near RHS Violet-Blue 94C flushed 94B. Fully opened: Inner surface: Near RHS Violet-Blue 90B. Outer surface: Near RHS Violet-Blue 94C flushed 94B. Fading: Inner surface: Near RHS Violet-Blue 90B. Outer surface: Near RHS Violet-Blue 94C flushed 94B.

Color:
*Lower lip*.—When opening: Inner surface: Near RHS Violet-Blue 90A. Outer surface: Near RHS Violet-Blue 94C flushed 94B. Fully opened: Inner surface: Near RHS Violet-Blue 90B. Outer surface: Near RHS Violet-Blue 94C flushed 94B. Fading: Inner surface: Near RHS Violet-Blue 90B. Outer surface: Near RHS Violet-Blue 94C flushed 94B.

Color:
*Throat*.—When opening: Near RHS Violet-Blue 94C with spots Greyed-Purple 187A. Fully opened: Near RHS Violet-Blue 94D with spots Greyed-Purple 187A.

Color:
*Tube*.—When opening: Inner surface: Near RHS Purple 76C. Outer surface: Near RHS Violet-Blue 92B. Fully opened: Inner surface: Near RHS Purple 76D. Outer surface: Near RHS Violet-Blue 92C. Fading: Inner surface: Near RHS Violet-Blue 91B. Outer surface: Between RHS Violet-Blue 91A and 91B.

Bud:
*Shape*.—Oblong.
*Length*.—6 mm.
*Diameter*.—3 mm.
*Color*.—Near RHS Violet-Blue 91B.

Bracts:
*Shape*.—Narrow deltate.
*Length*.—7 mm.
*Diameter*.—3 mm.
*Color*.—Near RHS Green 137C.
*Texture*.—Pubescent.

Calyx:
*Shape*.—Tubular.
*Length*.—Approximately 7 mm.
*Width*.—Approximately 3 mm.

Sepals:
*Quantity per flower*.—5.
*Unfused length*.—1 to 2 mm.
*Unfused width*.—1 to 2 mm.
*Margin*.—Lobed, tips acuminate.
*Apex*.—Acute.
*Base*.—Fused.
*Texture*.—Pubescent, all surfaces.
*Color, upper and lower surfaces*.—Near RHS Green 137D.

REPRODUCTIVE ORGANS

Stamens:
*Number*.—4.
*Filament length*.—Approximately 3 mm.
*Filament color*.—Near RHS Violet-Blue 91D.

Anthers:
*Shape*.—Globular.
*Length*.—Approximately 1 mm.
*Diameter*.—Less than 0.1 mm.
*Color*.—Near RHS Violet-Purple N92A.
*Pollen*.—Color: Near RHS White N155A. Quantity: sparse.

Pistil:
*Number*.—1.
*Length*.—Approximately 1.2 cm.
*Style*.—Length: Approximately 9 mm. Diameter: Approximately 1 mm. Color: Near RHS Violet 84C.
*Stigma*.—Shape: Cleft. Length: Approximately 1 mm. Color: Near RHS Violet 86A. Ovary color: Near RHS Green 137C.

OTHER CHARACTERISTICS

Disease and pest resistance: Not observed to be susceptible nor resistant to normal diseases and pests of *Nepeta faassenii*.

Temperature tolerance: USDA Zone 5b through 10.

Fruit/seed production: Not observed to date.

What is claimed is:

1. A new and distinct cultivar of *Nepeta* plant named 'G19213' as herein illustrated and described.

* * * * *